United States Patent [19]

Iskander

[11] Patent Number: 4,945,061
[45] Date of Patent: Jul. 31, 1990

[54] DISPOSABLE CULTURE DISH WITH REINFORCEMENT RIBS

[76] Inventor: Ezzat Iskander, 36 George Crescent, Caledon East, Ontario, Canada, L0N 1E0

[21] Appl. No.: 441,530

[22] Filed: Nov. 27, 1989

[51] Int. Cl.$^5$ ............................................. C12M 3/00
[52] U.S. Cl. .................................... 435/298; 435/301
[58] Field of Search ........................ 435/297, 298, 301

[56] References Cited

U.S. PATENT DOCUMENTS

| | | | |
|---|---|---|---|
| 2,874,091 | 2/1959 | Fisk | 435/298 |
| 3,165,450 | 1/1965 | Scheidt | 435/298 |
| 4,728,607 | 3/1988 | Dorn et al. | 435/301 |

*Primary Examiner*—Carroll B. Dority

[57] ABSTRACT

A Petri dish in which the flat bottom is provided with a plurality of preferably radial ribs is disclosed. The ribs do not project more than about 0.050 inches above the upper surface of the bottom, and preferably not more than about 0.030 inches. The thickness of the bottom portion other than at the ribs is not greater than about 0.030 inches, and preferably not greater than about 0.025 inches. Various rib arrangements are contemplated. In the preferred embodiment, there are at least three radial ribs, and preferably four ribs spaced at 90 degrees to each other. A lid having the same basic structure may also be produced. Generally any suitable rib layout could be selected. A large number of ribs could be provided, if desired, though not a requirement. The ribs need not necessarily be radial. The ribs need not necessarily be continuous, and they need not necessarily run all the way from the center to the side wall, or from side wall to side wall. The ribs need not necessarily be straight, but could be curved. The ribs could project downwardly instead of or in addition to upwardly.

19 Claims, 3 Drawing Sheets

DISPOSABLE CULTURE DISH WITH REINFORCEMENT RIBS

BACKGROUND OF THE INVENTION

This invention relates to Petri dishes.

Petri dishes are well known and in common usage, particularly in laboratories for producing cultures in a culture medium such as agar. Such dishes have a flat bottom portion and short cylindrical sides. Flatness of the bottom portion is important, so that a uniform layer of the culture medium can be produced using as little of the medium as possible.

The market for Petri dishes is highly competitive and price sensitive. It is therefore encumbent on manufacturers to produce Petri dishes at as low a price as possible. At the same time, however, it is of course essential that the quality of the product be excellent.

In Petri dishes, curvature of the bottom is a problem because the bottom tends to develop significant curvature after removal from the mold, especially due to rapid cooling caused by the relatively fast cycle times in production. Curvature is unacceptable because it confuses accurate assessment of the culture in the dish. This problem traditionally has been dealt with by thickening the walls of the dish and increasing the cooling time before it is ejected from the mold. However, these solutions are unsatisfactory because they involve the use of more material than strictly required for the mechanical strength of the finished article, and they lengthen the mold cycle time, thereby making the process expensive while lowering the production rate of the mold.

In general, there is a need for an improved Petri dish, such that manufacturing costs can be reduced and quality either enhanced or at the very least not sacrificed.

Since the cost of materials, i.e. resins, is the primary cost factor in producing Petri dishes, the best way to reduce cost is to reduce the amount of material required. However, it has not hitherto been possible to reduce the amount of material to the extent possible in the present invention, without sacrificing quality.

"Quality" in this context means primarily that the Petri dish must be reasonably strong, and that the bottom must be as close as possible to being absolutely flat. Other factors include transparency and the ability of agar to bond to the dish.

SUMMARY OF THE INVENTION

It is an object of the invention to provide a reduced cost Petri dish with the quality being enhanced or at the very least not reduced.

Thus in accordance with the present invention there is provided a Petri dish having the usual flat bottom portion and shallow cylindrical sides. In the invention, the bottom is provided with a plurality of preferably radial ribs, the upwardly projecting portion of the ribs, if any, projecting not more than about 0.050 inches above the upper surface of the bottom, and preferably not more than about 0.020 inches. The thickness of the bottom portion other than at the ribs is not greater than about 0.030 inches, and preferably not greater than about 0.025 inches.

Various rib arrangements are contemplated.

The ribs result in a very flat bottom surface despite the rapid cooling brought about by short cycle times, thus avoiding the problems of the prior art tendency for the bottom portion to become curved. The ribs also permit the Petri dishes to be manufactured using much less resin than in the prior art.

Further features of the invention will be described or will become apparent in the course of the following detailed description.

BRIEF DESCRIPTION OF THE DRAWINGS

In order that the invention may be more clearly understood, the preferred and alternative embodiments thereof will now be described in detail by way of example, with reference to the accompanying drawings, in which.

DETAILED DESCRIPTION OF THE PREFERRED EMBODIMENTS

Figure 1:
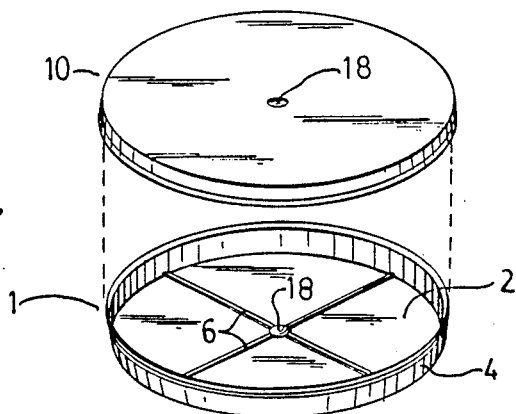
FIG. 1 is a perspective of one embodiment, showing both the Petri dish and a lid.
Figure 2:
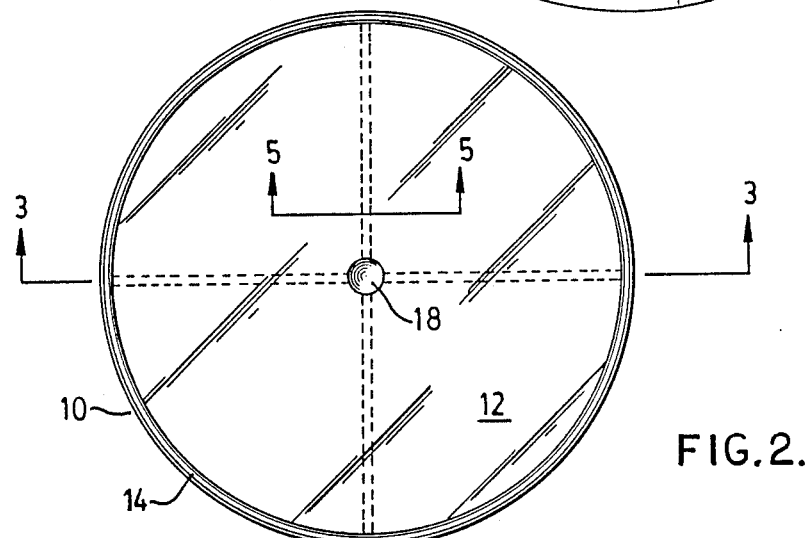
FIG. 2 is top view of the lid.
Figure 3:
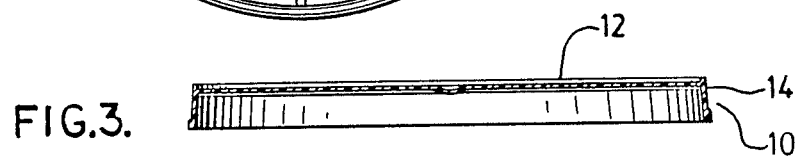
FIG. 3 is a cross-section of the lid.
Figure 4:
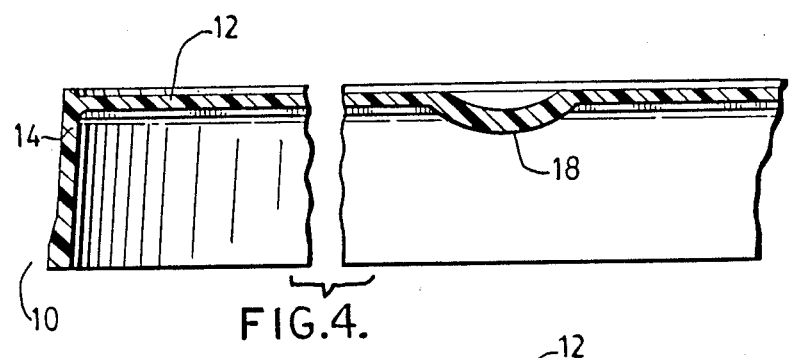
FIG. 4 is a more detailed cross-section of the lid.
Figure 5:
FIG. 5 is a cross-section showing one of the ribs in the lid.
Figure 6:
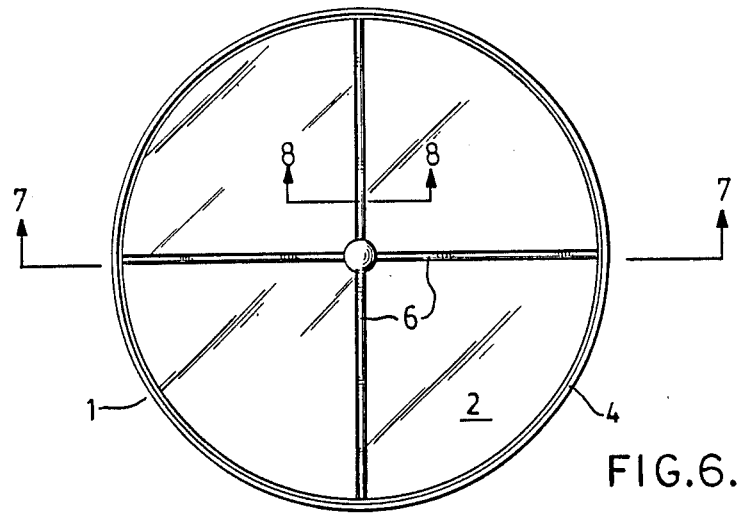
FIG. 6 is a top view of the dish.
Figure 7:
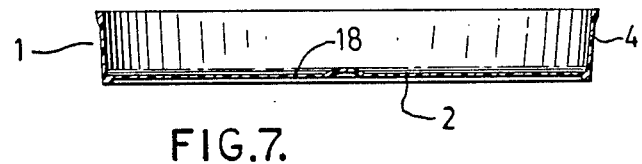
FIG. 7 is a cross-section of the dish.
Figure 8:
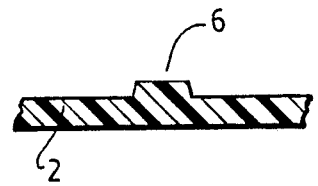
FIG. 8 is a cross-section of one of the ribs of the dish.
Figure 9:
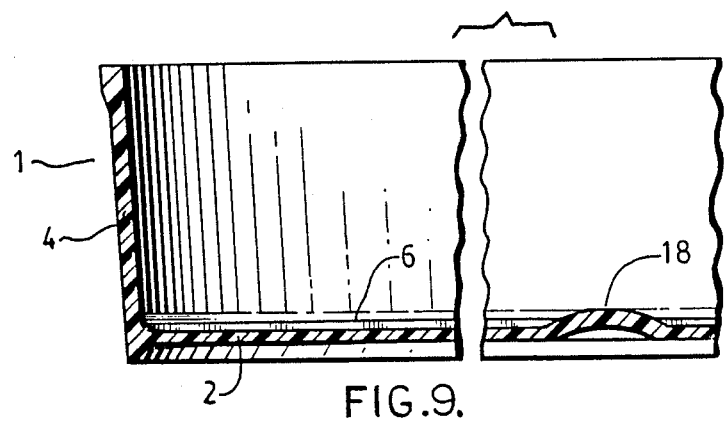
FIG. 9 is a more detailed cross-section of the dish.
Figure 10:
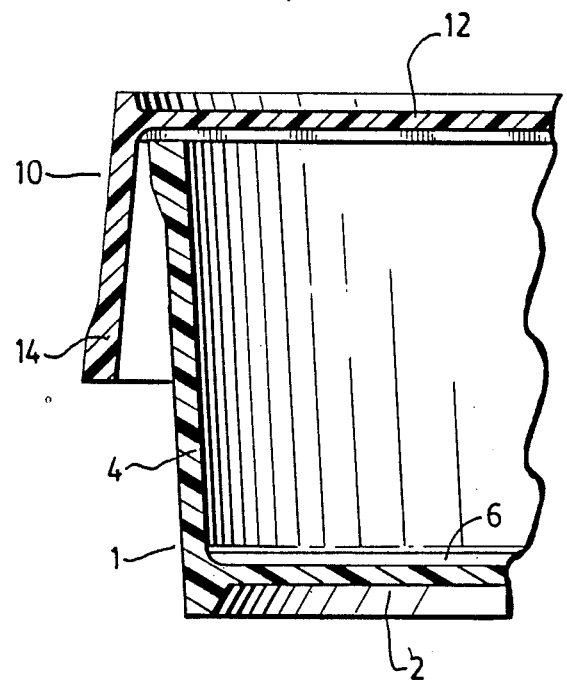
FIG. 10 is a cross-section showing the lid positioned on the dish.

Referring to the drawings, the Petri dish 1 has a substantially flat horizontal bottom portion 2 and a short substantially cylindrical side wall 4 integral with and around the bottom portion. The bottom portion is provided with a plurality of ribs 6, preferably but not essentially radially oriented, and not exceeding about 0.050 inches in height and preferably not exceeding about 0.030 inches in height, above the upper surface of the bottom. The thickness of the bottom portion other than at the ribs is not greater than about 0.030 inches, and preferably not greater than about 0.025 inches.

The ribs ensure that the bottom portion remains substantially flat on removal from the mold and thereafter. The ribs provide greater rigidity for the bottom portion than would otherwise be the case with such a thin section.

In one embodiment of the dish 1, shown in FIGS. 1 and 6–10, there are four radial ribs 6, spaced at 90 degrees to each other. There of course could be more than the basic four ribs, evenly distributed around the area of the bottom portion. A practical minimum would be three ribs, each 120 degrees from the other.

A lid 10 for the Petri dish may be produced according to the same principles, as illustrated in FIGS. 1–5 and 10. The lid is of very similar construction, including a top portion 12, a side wall 14, and ribs 6.

Figure 11:
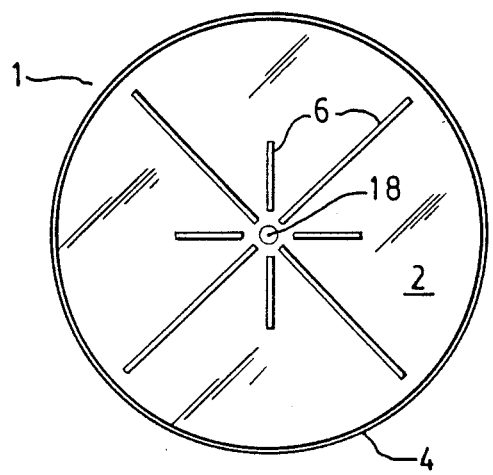
FIG. 11 is a top view of one alternative rib configuration.

In an alternative embodiment, shown in FIG. 11, there are eight ribs, namely four ribs 6 preferably being at least about 0.9 R, where R is the radius of the bottom portion, the ribs being spaced at 90 degrees to each other, and four ribs 14 preferably being at least about 0.25 R running from near the center of the bottom portion, and being spaced at 90 degrees from each other, offset by 45 degrees from the first four ribs. At present, this embodiment is preferred for the dish, with the four rib configuration being preferred for the lid, although either could be used for either the dish or the lid. Again, there of course could be more than the basic eight ribs of this embodiment, evenly distributed around the area of the bottom portion.

In yet another alternative embodiment, not specifically illustrated but merely exemplary of one of many possible variations, there could be at least about sixteen ribs, the majority of which are not greater in length than about 0.25 R. The ribs could be evenly distributed around the area of the bottom portion.

In each of the embodiments, there may or may not be a dimple 18 at the center of the bottom portion, depending on the location of the injection gate. The gate may be in the center of the bottom, at the bottom offset from the center, or at the side wall. In the preferred embodiment, FIGS. 1 and 6–10, the ribs run from the dimple to the side wall, although there is no reason why the ribs could not stop short of the dimple and/or side wall.

The various key dimensions in the preferred embodiment of FIGS. 1 and 6–10, for a Petri dish of 3.3 inch nominal diameter, are as follows:

| | |
|---|---|
| Bottom portion thickness: | 0.018 inch |
| Rib total height: | 0.030 inch |
| Rib height above upper surface of bottom: | 0.012 inch |

Obviously, these dimensions could be varied somewhat without departing from the principles of the invention, and could be scaled up or down appropriately for larger or smaller Petri dishes with only routine testing and experimentation being required for optimization.

Table 1 below shows some of the characteristics of prototype Petri dishes produced according to the invention:

TABLE 1

| Petri Dish Resin | Weight (g) | Thickness (in) | Flatness ($10^{-3}$ in) | Base Load (kg) | Base Stiff kg/mm | Side Stiff. kg/mm | Twist Stiffness ft/lb cu in |
|---|---|---|---|---|---|---|---|
| Ribbed Prototype 615APR | 8.44 o = 0.06 | 0.019 | 5.27 o = 2.14 | 41.6 o = 2.3 | 15.1 o = 0.05 | 5.0 o = 0.08 | 29.90 o = 10.5 |
| Ribbed Prototype 688 | 8.66 o = 0.05 | 0.021 | 1.95 o = 1.8 | 25.2 o = 9.6 | 11.3 o = 3.3 | 6.5 o = 1.2 | 24.90 o = 15.7 |

Note: Weight is combined weight of base plus lid; other columns are for base only.

It will be appreciated that the embodiments described in the text above are by way of example only. Many variations on the invention will be obvious to those knowledgeable in the field, and such obvious variations are within the scope of the invention as described and claimed, whether or not expressly described.

For example, it should be emphasized that generally any suitable rib layout could be selected, it being a matter of routine testing of prototypes to determine whether or not a given rib layout is acceptable from a strength viewpoint. A large number of ribs could be provided, if desired, though a large number is not a requirement. The ribs need not necessarily be radial, although that is preferable. The ribs need not necessarily be continuous, i.e. they could be "broken", and they need not necessarily run all the way from the center to the side wall, or from side wall to side wall. The ribs need not necessarily be straight, but could be curved.

Furthermore, although the above embodiments describe ribs which project upwardly from the upper surface of the bottom of the dish, it should be readily apparent that the ribs could project downwardly from the underside of the dish, or some could project upwardly and others downwardly, or individual ribs could project both upwardly and downwardly (e.g. the bottom of the dish could be in effect centered on the overall height of the rib). The height of the ribs above the upper surface of the bottom should still not exceed the above-mentioned heights, and indeed may be zero in the case of ribs which project only downwardly.

WHAT IS CLAIMED AS THE INVENTION IS:

1. In a Petri dish having a substantially flat horizontal bottom portion and a short substantially cylindrical side wall integral with and around said bottom portion, the improvement in which said bottom portion is provided with a plurality of upwardly projecting ribs, the upwardly projecting portions of said ribs, projecting not more than about 0.050 inches above the upper surface of said bottom, and in which the thickness of said bottom portion other than at the ribs is not greater than about 0.030 inches.

2. The improvement as recited in claim 1, in which there are at least three radial ribs, each not less than about 0.9 R in length, where R is the radius of the bottom portion, and in which said ribs are evenly distributed around the area of the bottom portion.

3. The improvement as recited in claim 1, in which there are four radial ribs, each not less than about 0.9 R in length, where R is the radius of the bottom portion, and in which said ribs are spaced 90 degrees from each other.

4. The improvement as recited in claim 1, in which there are at least about 16 ribs, the majority of which are not greater in length than about 0.25 R, where R is the radius of the bottom portion, and in which said ribs are evenly distributed around the area of the bottom portion.

5. The improvement as recited in claim 1, in which there are at least eight radial ribs, each being at least about 0.5 R, where R is the radius of the bottom portion, and in which said ribs are evenly distributed around the area of the bottom portion.

6. The improvement as recited in claim 5, in which there are eight ribs, namely a first four ribs being at least about 0.9 R, where R is the radius of the bottom portion, said first four ribs being spaced at 90 degrees to each other, and a second four ribs being at least about 0.25 R running from near the center of the bottom portion, and being spaced at 90 degrees from each other, offset by 45 degrees from said first four ribs.

7. The improvement as recited in claim 1, in which said ribs project not more than about 0.030 inches above the upper surface of said bottom.

8. The improvement as recited in claim 2, in which said ribs project not more than about 0.030 inches above the upper surface of said bottom.

9. The improvement as recited in claim 3, in which said ribs project not more than about 0.030 inches above the upper surface of said bottom.

10. The improvement as recited in claim 4, in which said ribs project not more than about 0.030 inches above the upper surface of said bottom.

11. The improvement as recited in claim 5, in which said ribs project not more than about 0.030 inches above the upper surface of said bottom.

12. The improvement as recited in claim 6, in which said ribs project not more than about 0.030 inches above the upper surface of said bottom.

13. The improvement as recited in claim 1, in which the thickness of said bottom portion other than at the ribs is not greater than about 0.025 inches.

14. The improvement as recited in claim 2, in which the thickness of said bottom portion other than at the ribs is not greater than about 0.025 inches.

15. The improvement as recited in claim 3, in which the thickness of said bottom portion other than at the ribs is not greater than about 0.025 inches.

16. The improvement as recited in claim 4, in which the thickness of said bottom portion other than at the ribs is not greater than about 0.025 inches.

17. The improvement as recited in claim 5, in which the thickness of said bottom portion other than at the ribs is not greater than about 0.025 inches.

18. The improvement as recited in claim 6, in which the thickness of said bottom portion other than at the ribs is not greater than about 0.025 inches.

19. The improvement as recited in claim 1, in which said bottom portion includes a plurality of downwardly projected ribs.

* * * * *